Figure 1:
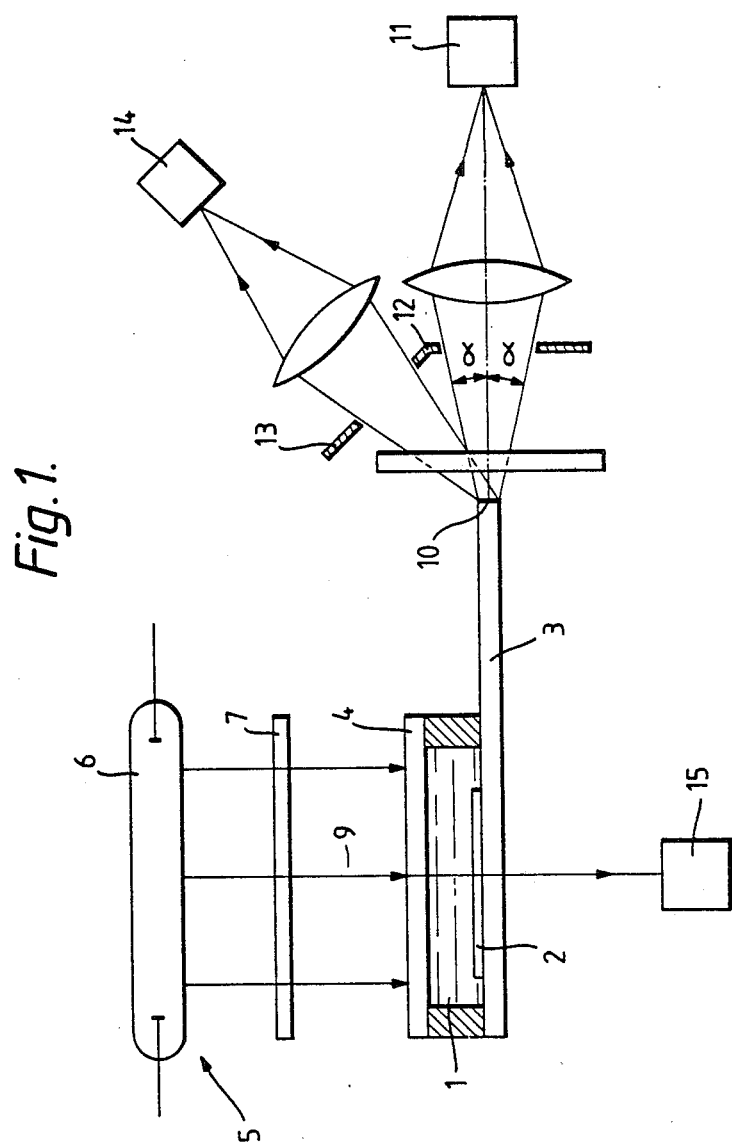

United States Patent [19]

Shanks et al.

[11] Patent Number: 4,810,658
[45] Date of Patent: Mar. 7, 1989

[54] PHOTOMETRIC INSTRUMENTS, THEIR USE IN METHODS OF OPTICAL ANALYSIS, AND ANCILLARY DEVICES THEREFOR

[75] Inventors: Ian A. Shanks; Alan M. Smith, both of Bedford, England

[73] Assignee: Ares-Serono Research & Development, Boston, Mass.

[21] Appl. No.: 829,647

[22] PCT Filed: Jun. 12, 1985

[86] PCT No.: PCT/GB85/00257
§ 371 Date: Feb. 13, 1986
§ 102(e) Date: Feb. 13, 1986

[87] PCT Pub. No.: WO86/00135
PCT Pub. Date: Jan. 3, 1986

[51] Int. Cl.⁴ .................................... G01N 21/64
[52] U.S. Cl. .................... 436/172; 250/227; 356/244; 356/440; 422/68; 422/73
[58] Field of Search .......... 356/244, 440; 250/227; 422/68, 73; 436/800, 805, 172

[56] References Cited

U.S. PATENT DOCUMENTS

| | | | |
|---|---|---|---|
| 3,939,350 | 2/1976 | Kronick et al. | 250/365 |
| 3,975,084 | 8/1976 | Block | 356/244 X |
| 4,175,864 | 11/1979 | Gilby | 356/244 X |
| 4,181,441 | 1/1980 | Noller | 356/414 |
| 4,303,859 | 12/1981 | McCue | 356/244 X |
| 4,582,809 | 4/1986 | Block et al. | 250/227 X |
| 4,595,833 | 6/1986 | Sting | 356/353 |
| 4,602,869 | 7/1986 | Harrick | 356/244 |
| 4,608,344 | 8/1986 | Carter et al. | 436/34 |

FOREIGN PATENT DOCUMENTS 75353  3/1983  European Pat. Off. .

OTHER PUBLICATIONS

Harrick, Analytical Chemistry 45(4), pp. 687–691.
Chabay, Analytical Chemistry 54(9), pp. 1071(A)–1080(A).
Lee, et al., Applied Optics 18(6), pp. 862–868.

Primary Examiner—Barry S. Richman
Assistant Examiner—Jill Johnston
Attorney, Agent, or Firm—Cushman, Darby & Cushman

[57] ABSTRACT

A method of optical analysis of a test sample which comprises a sample material with light-absorbing, scattering, fluorescent, phosphorescent or luminescent properties, which sample is partly in a liquid phase and partly bound to an adjacent solid surface, to discriminate the respective parts of said sample material which are located in the liquid and bound to said solid surface: comprising the steps of providing as said solid surface a surface of a transparent solid optical waveguide, and measuring light from the sample material bound to said solid surface that has passed into and through said transparent solid optical waveguide with total internal reflections and emerged from said waveguide at an angle that deviates from the optical axis of said waveguide by an angle appreciably less than $\alpha$, where $$\alpha = \arcsin\sqrt{(n_2^2 - n_1^2)}$$

where $n_2$ is the refractive index of the material of the waveguide and $n_1$ is the refractive index of the adjacent liquid, the excluding from said measurement substantially all light that has emerged from said waveguide at an angle that deviates from said optical axis by $\alpha$ or more.

3 Claims, 5 Drawing Sheets

PHOTOMETRIC INSTRUMENTS, THEIR USE IN METHODS OF OPTICAL ANALYSIS, AND ANCILLARY DEVICES THEREFOR

This invention relates to improvements in photometric instruments, and their use in methods of optical analysis, and in ancillary devices for use therewith.

The prior art contains numerous disclosures of analytical devices for handling and metering small volumes of test samples.

G.B. No. 2 090 659 (Instrumentation Laboratory, Inc.) describes test strips constructed with a self-filling metering channel and a lip or inlet on which a sample of more than about 10 microliters of for example whole blood can be placed, so that (for example) 10 microliters is taken up by capillary action to react with a reagent carried on a fibrous pad above a filter layer beneath a transparent window. The result can be viewed by the unaided eye, e.g. as a colour reaction.

G.B. Nos. 2 036 075 (H. E. Mennier), 1 104 774 (J. P. Gallagher), EP Nos. 0 057 110, 0 034 049, 0 010 456 (Kodak), all describe some other aspect of the uses of capillary channel or chamber dimensions for handling biological or test fluids.

G.B. No. 1 530 997 (Monsanto) describes the use of coated optical fibres which can be used in tests that change the light transmitting capabilities of the waveguides via reactions. WO No. 81/00912 (Buckles) also describes fibre-optical devices in which the fibre surface or surrounding modify the light transmission through the core.

U.S. Pat. No. 3,939,350 describes optical measurement of fluorescent material bound to the surface of a solid transparent prism by a method involving a single total internal reflection and interaction of the evanescent wave at the surface of the prism with the bound material.

EP No. 0 075 353 (Battelle) makes specific reference to the exponentially-decaying (evanescent) external radiation due to light which is propagated longitudinally in a fibre, and its interaction with coatings, and this principle is also taken up in immunoassay test devices of EP No. 0 103 426 (Block) in which light of fluorescence excitation as well as emission wavelengths is propagated within a antigen—or antibody—coated optical fibre or plate contacting a capillary-dimensional sample liquid volume bounded by a tube or another plate and containing a fluorescent-tagged binding partner of the material coated on the fibre or plate.

It is an aim of the present invention to provide instrumental arrangements by which very small liquid samples can be optically analysed in a convenient and flexible manner to discriminate sample material which is bound to a solid surface from sample material that remains free in solution.

According to the present invention we provide methods and instrumental arrangements for carrying out immunoassays or other chemical or biological tests, in the course of which a material with light-absorbing or fluorescence or luminescence properties becomes bound to the surface of a transparent solid body (especially from a solution or dispersion contacting the solid body), for example a prism, sheet or fibre, to a variable extent depending on the presence or amount of an analyte under test. In these arrangements the transparent solid body is optically coupled to a photodetector in such a way that the light path from the material to the detector passes through the solid body and may be therein totally internally reflected once or a plurality of times, i.e. the solid body acts as an optical waveguide. Usually the detector yields an electrical output signal which is processed and used in per se known manner not in itself constituting this invention, to yield a signal or indication representative of a parameter of interest in connection with the test. The arrangement includes a diaphragm or other limitation of the angle of view of the detector in order to ensure that substantially only that light is detected which comes from material which is bound to the surface of the transparent solid body. The transparent solid body acts as a waveguide for the light which comes from the surface-bound material, and which can pass by for example transmission, scattering, reflection, luminescence, fluorescence, or phosphorescence, (for practical purposes herein considered as a form of fluorescence). The diaphragm or other limitation of the angle of view of the detector ensures that light from otherwise similar material that remains in solution or dispersion and thereby remains spaced from the surface of the transparent solid body, is not also detected to an appreciable extent. It is within the scope of the invention to arrange that the detector receives light preferentially from the bound material, together with a certain amount of light from the solution or dispersion, and then to provide a compensatory signal from another detector arranged to receive light from the two sources in a different proportion, e.g. substantially all from the solution or dispersion. The invention also extends to alternative arrangements in which the restriction on the angle of view of the detector is the inverse of that already described, namely so that the principal detector receives light substantially only, or at least preferentially, from the solution or dispersion.

Accordingly, in one aspect the invention comprises a method of optical analysis of a test sample which comprises a sample material with light-absorbing or fluorescent, phosphorescent or luminescent properties, which sample is partly in a liquid phase and partly bound to an adjacent solid surface, to discriminate the respective parts of said sample material which are located in the liquid and bound to said solid surface: comprising the steps of providing as said solid surface a surface of a transparent solid optical waveguide, and measuring light from the sample material bound to said solid surface that has passed into and through said transparent solid optical waveguide with total internal reflections and emerged from said waveguide at an angle that deviates from the optical axis of said waveguide by an angle appreciably less than $\alpha$ where $$\alpha = \arcsin \sqrt{(n_2{}^2 - n_1{}^2)}$$

where $n_2$ is the refractive index of the material of the waveguide and $n_1$ is the refractive index of the adjacent liquid (generally less than $n_2$), and excluding from said measurement substantially all light that has emerged from said waveguide at an angle that deviates from said optical axis by $\alpha$ or more.

In another aspect the invention comprises a combination of a photometric instrument and a test object adapted therefor, suitable for example for carrying out immunoassays or other chemical or biological tests, comprising (i) a test object such as a slide or cell received and located at a test object location, for containing a sample material with light-absorbing or fluorescence or luminescence properties, said test object comprising a transparent solid body, e.g. a prism, sheet or fibre, to act as a waveguide, and to the surface of which the sample material can become bound from a solution or liquid dispersion contacting the solid body;

(ii) a photodetector arranged so that when a test object is at the test object location (the "in use" condition) the transparent solid body is optically coupled to the photodetector, so that light propagating in the transparent solid body can be received by the photodetector after its emergence;

(iii) (optionally) a light source arranged so that in the "in use" condition it can illuminate the test material with light (for example at some transverse angle to the principal direction of propagation of the light in the waveguide, eg. at or about 90°), so that light from the test material passes into and through the solid body, via total internal reflections, to the detector; and (iv) a diaphragm or other limitation of the angle of view of the detector in order to discriminate that light which comes from material which is bound to the surface of the waveguide, e.g. either by transmission, scattering, reflection, luminescence or fluorescence, from light from otherwise similar material that remains in solution or dispersion and thereby remains spaced from the surface of the transparent body, said limitation of the angle of view corresponding to an angle $\alpha$ as defined above.

The invention is considered to rely on the difference in the angular range of directions of propagation within which the light emerging from the solid body is distributed, depending on whether the light comes from the liquid or from a very thin surface bound layer. The solid body can be an optical fibre or sheet such as a flat solid slide, of glass, silica, inorganic crystal (eg. sapphire) or plastics material (eg. acrylic plastics polycarbonate, or polystyrene), and in that case, light from material in an adjacent liquid of relatively low refractive index, e.g. close to that of water, emerges at rather large angles off the axis of the fibre or plane of the sheet. As the refractive index of the bound layer from which the light comes is the larger and closer to the refractive index of the solid body, the larger is the angular range of distribution of the light: this range now includes angles closer to the axis of the fibre or plane of the sheet. Furthermore, fluorescent or luminescent molecules or scattering molecules or particles closely adherent to the surface of the transparent solid can emit light into an angular range (corresponding to the guided modes of the substrate) part of which would be a "forbidden" range in the context of ray optics, into which only an evanescent wave extends and not the main propagated light from sources located in the body of the liquid, e.g. aqueous liquid. This can result in light that emerges from the fibre or sheet at exit angles relatively close to the axis.

We find that where a solid slide or other waveguide is in contact with an adjacent aqueous liquid containing a fluorescent solute, and fluorescence is excited by a light source transverse to the axis of the waveguide or plane of the slide, then the fluorescence emerging from the end of the waveguide or slide exits mainly at angles of at least about $\alpha = \arcsin\sqrt{(n_2^2 - n_1^2)}$ where $n_2$ represents the refractive index of the waveguide or slide and $n_1$ represents the refractive index of the liquid. For acrylic plastics material, water, and yellow-green fluorescence at 510 nm, $\alpha$ can be about 41°. Thus most of the light will emerge at angles off-axis by 41°-90° in either sense and relatively little at angles less than about 40° in either sense.

In the presence of an adsorbed fluorescent layer at the surface of the slide or other waveguide, more of the fluorescent light emerging from the end of the slide or waveguide will emerge at angles closer to the axis. However, rather little difference is found in the amount of light emerging within a few degrees, about 5° in either direction, of the axis itself.

In the case of a glass slide or waveguide and an aqueous solution, and fluorescent light of 510 nm wavelength, the corresponding angle $\alpha$ falls at about 47° off-axis, so that if desired light from dissolved fluorophor can be detected conveniently in the range above about 49°-52° and up to 90° in either direction off the axis. Light from an adsorbed layer can be distinguished by its emergence over a wider range of exit angles including smaller angles less than about 47°. Thus it can be detected conveniently at angles in the range 5°-45° in either direction off the axis.

A low background light level may be detected to a certain extent over a wide angular range, especially close to the axis and up to about 5° off axis in either direction.

The effects of background light in the instrumental arrangements described herein can be dealt with in any of a number of ways. Background light is found to arise from stray exogenous light, and in the case of examples of the invention that use a light source to excite luminescence, eg. fluorescence, it can happen that scattered source light and background fluorescence from materials other than the wanted sample materials may be liable to find their way to the detectors. Examples of suitable filter arrangements to exclude light of other than the wanted wavelengths are illustrated below.

Background light in the region within the range of $\pm \alpha$ on either side of the axis can be detected for example (a) by providing a separate detector to capture only light emerging along the axis or within a narrow angular range eg. $\pm 5°$ on either side of the axis and to use the output of such a detector as an index of background light, (b) to measure the light emerging within the angular range up to not more than $\pm \alpha$, (usually a few degrees less, as described above,) at the wavelengths of the light source, and to use this measure as an index of the background component of the light emerging within a similar angular range at wavelengths to which the principal detector arrangement is sensitive. Simpler measures are usually enough in the case of arrangements for detecting bioluminescent or chemiluminescent emission, since a source of excitation light is absent: a light-tight optical enclosure is generally enough to deep the background down.

Suitable diaphragms can be arranged as may be desired to select emergent light of any angle of emergence or range of angles of emergence. In the case of a circular-section glass or plastics waveguide surrounded by liquid the diaphragms can be circular or annular diaphragms; and in the case of a waveguide in the form of a flat slide the diaphragms can be of rectangular or slit form.

A preferred form of the invention is one in which a fluorescent material in a liquid adjacent to a transparent waveguide such as a slide or fibre of for example glass or plastics is excited by light from a light source transverse to the axis or direction of propagation of light in the waveguide: light emerging from the end of the waveguide passes through a diaphragm or other restriction of the angle of view of a subsequent photodetector, by which the light emerging at angles less than $\alpha$ may be distinguished from the light emerging at angles greater than $\alpha$.

The aqueous liquid in this case can contain reagents and the surface of the waveguide can have a sensitisation such as a ligand-binding eg. immunosorbent sensitisation, which together correspond to any known suitable test such as a ligand binding assay, eg. immunoassay, that results in a variable degree of deposition or binding of fluorescent material to the sensitised surface, depending on the presence or quantity of an analyte under test. In this way the optical arrangements described herein can distinguish the degree of deposition or binding without the need for manipulations leading to physical separation of the free and bound material.

An alternative form of the invention, more suitable for colorimetric than fluorimetric or luminescence measurements, employs a light source that launches light longitudinally into a waveguide such as a fibre or slide of for example glass or plastics material, with a wide range of angles of incidence, e.g. through a diffuser, or alternatively with a selected narrower range of angles of incidence chosen to co-operate with the light-absorbing arrangements described next below: adjacent to the waveguide is a liquid containing light-absorbing material and reagents by which an amount of the light-absorbing material can become bound or deposited on the surface of the waveguide. In the presence of binding, attenuation occurs particularly of the light travelling in the waveguide with angles corresponding to emergence angles less than $\alpha$. The absorbing substances in the body of the liquid exert their attenuating effects on light that emerges at angles greater than $\alpha$. Suitable arrangements of diaphragms or restrictions on the angle of view of a photodetector arranged to detect the emergent light can then be provided to discriminate the light affected by the attenuation.

This arrangement has the aim of achieving an optical distinction between free and bound portions of a material that becomes partly bound to a solid phase, as is normally the case with many varieties of immunosorbent assay. But the present method achieves this distinction without requiring an actual physical separation of the liquid and solid phases (which are of lower and higher refractive index respectively) such as is normally required in an immunosorbent assay.

The arrangements described herein are suitable to be applied to bound sample material which interacts with light in any of a number of ways, especially for example by absorbance, scattering, fluorescent or phosphorescent emission, or chemiluminescent or bioluminescent emission. The chemical features of analytical test methods that exploit these interactions are known in the art and per se do not constitute this invention.

The invention is further illustrated by way of example by the following description and accompanying drawings.

Figure 2:
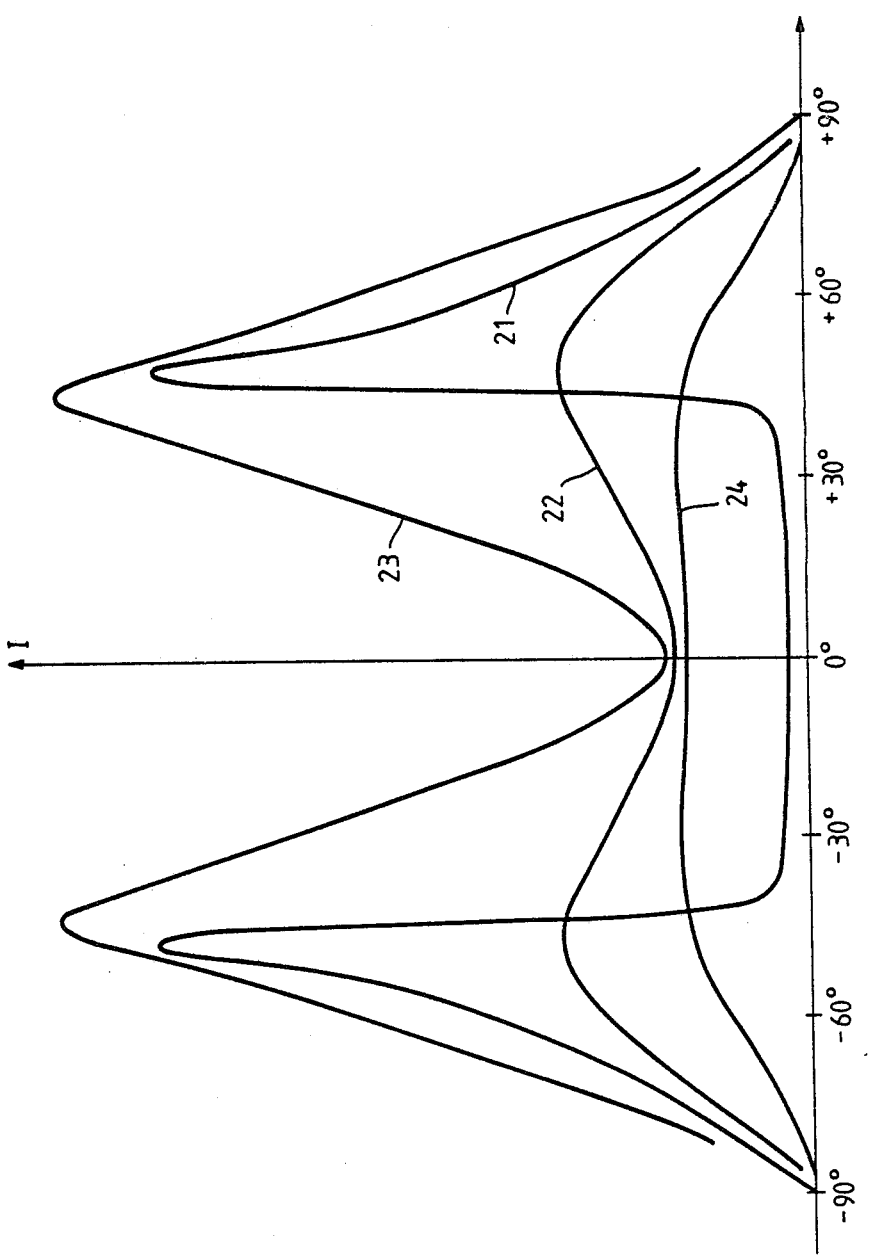
Figure 3:
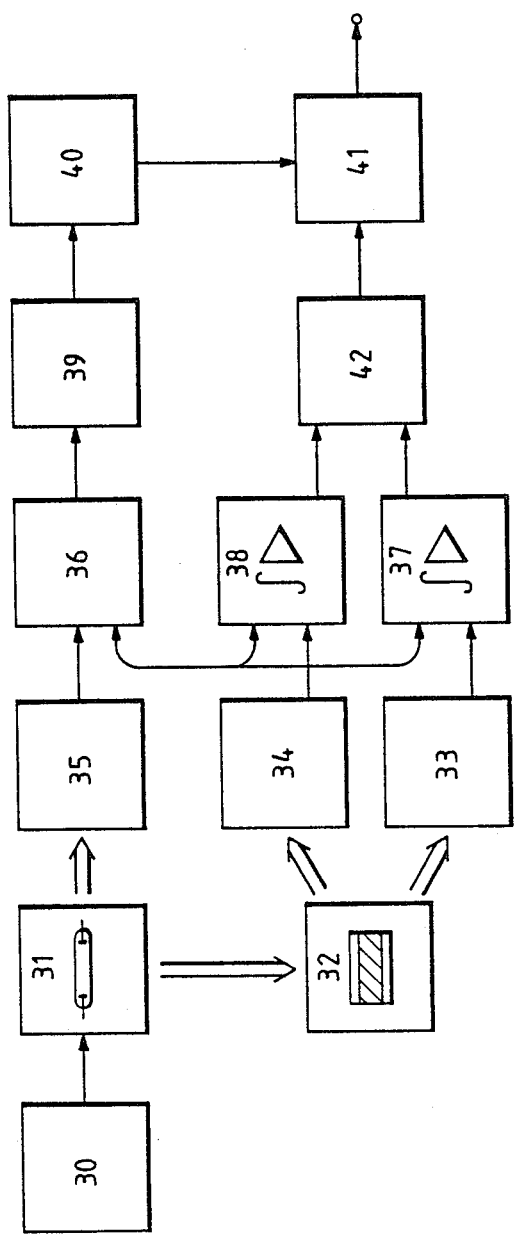
Figure 4:
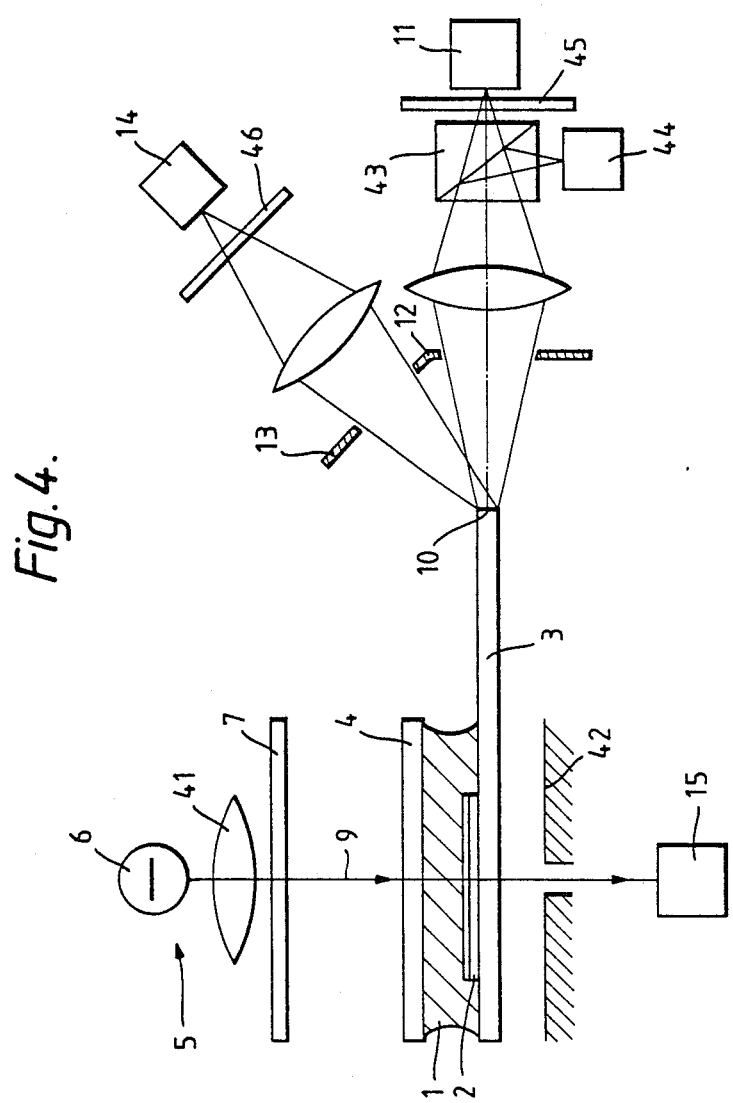
Figure 4A:
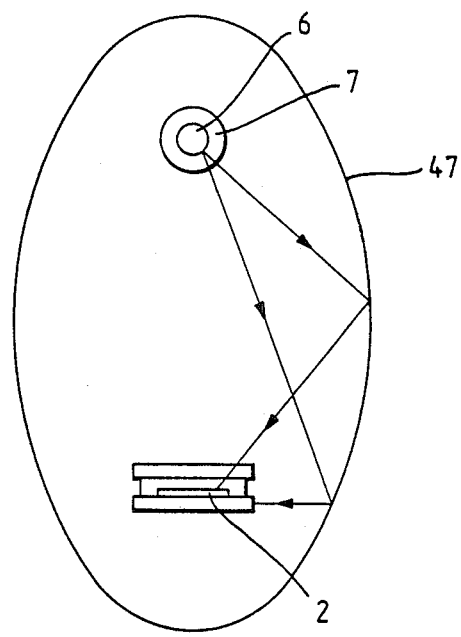
Figure 4B:
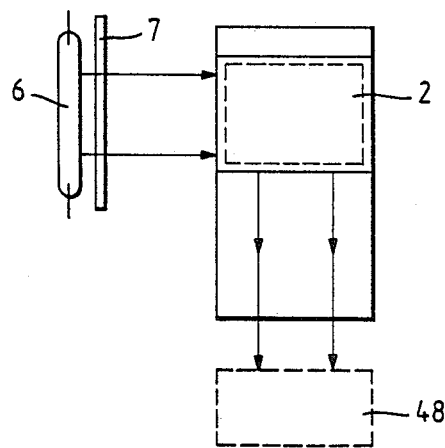

FIG. 1 of the drawings diagrammatically shows optical arrangements of one embodiment of the invention. FIG. 2 shows in diagrammatic graphical form the variation of light output with exit angle in an arrangement such as that of FIG. 1. FIG. 3 gives a block diagram of signal processing arrangements in an optical instrument as in FIG. 1. FIGS. 4, 4a and 4b show in diagrammatic scheme alternative optical arrangements usable according to the invention.

FIG. 1 shows, in fragmentary schematic cross-section, an arrangement according to an embodiment of the invention, for carrying out optical analysis of a specific binding reaction, e.g. an immunosorption reaction, taking place in a layer of aqueous sample liquid 1, by which a component, e.g. a fluorescent component with optical properties corresponding to fluorescein, of the material dissolved or dispersed in the liquid becomes partly bound in a layer 2 (shown with much exaggerated thickness in the drawing) at the surface of a solid transparent glass, silica or plastics slide or plate 3. Liquid 1 is located between plate 3 and a second parallel cover plate 4, which in the example illustrated is transparent but may be opaque with other instrument configurations. Plates 3 and 4 can form an integrated sample carrier, e.g. as described in our copending UK patent application No. 8415018, and copending application of June 13, 1985. The system is illuminated by a light source indicated schematically at 5 and comprises a flashlamp e.g. as often used in photoflash or stroboscopic flash units 6, and a filter 7 for selective transmission of light of excitation wavelength, to give a light output 9 illuminating the surface of transparent plate 4 and thereby also the liquid layer 1 and bound material 2. It can be preferable to space the lamp and filter as close as possible to the sample carrier so long as stray light paths from source to detector are guarded against.

In an alternative arrangement the plates and liquid and bound layers can be inverted relative to what is shown in FIG. 1 so that the light 9 impinges first on the equivalent of plate 3, then layer 2 and liquid 1. A mirror may be placed on the side of the sample cell opposite to the light source to increase the effective illumination.

In other alternative arrangements the light source shown can be replaced by any convenient, e.g. collimated and filtered, light source, or by a laser.

Alternative possible forms of light source can give a.c.-modulated light, e.g. chopped or pulsed light, as can be provided either by electronic control or by a segmented rotating chopper vane, according to component techniques well known in themselves.

Plate 3 is optically clear transparent with parallel plane faces and it has an end 10 which is substantially smooth and perpendicular to the long dimensions. The other edges can be made roughened and blackened to remove stray light.

Light from the liquid 1 and bound layer 2 travels (in part) along the length of plate 3 undergoing multiple reflections on the way, and emerges at end 10.

A photodetector 11 is arranged to receive and sense light propagating in plate 10 as totally internally reflected light, as in the equivalent of an optical fibre or waveguide, and emerging from end 10, but only receives light having an exit angle which diverges by not more than an angle $\alpha$ as indicated in FIG. 1, measured relative to an axis direction parallel to the long dimension of plate 3. In other words, light that diverges from the axis at an angle greater than $\alpha$ is not to be caught by detector 11. This is achieved by screening arrangements including apertured diaphragm 12, placed far enough away from end 10 of plate 3 so that it makes a practically inappreciable difference ($\leq$about 2°-3°) to the angle whether the light emerges from the top or bottom of end 10. It can be useful to associate the apertured diaphragm with a convex lens, eg. a cylindrical lens, to collect the light exiting over the desired angular range on to the photodetector.

The angle $\alpha$ is chosen in such a way that it is less than the value $$\arcsin\sqrt{(n_2^2 - n_1^2)}$$

by an amount sufficient to exclude practically all the light that arises from the liquid 1 rather than from the layer 2. In the above trigonometrical formula $n_1$ represents the refractive index of the liquid 1 and $n_2$ represents the refractive index of the solid substrate, i.e. the plate 3. For the case of fluorescent yellow-green light around 510 nm and a substrate 3 of acrylic plastics material, ($n_2$ about 1.495), used in connexion with an aqueous solution, the value of the formula is about 41°, and we find that a suitable corresponding value for $\alpha$ is in practice about >4° less than this value, e.g. in this case about 37° or less, preferably only a little less. It is not desirable to set $\alpha$ very much smaller than necessary because then there is a risk of excluding light arising from bound layers which have a refractive index not much greater than that of the surrounding liquid, or are slightly spaced off (on a molecular scale) from the surface.

In this way detector 11 receives light preferably from the material bound to the waveguide surface, though some of the light from this material is of course lost in other directions.

Additional detectors are in this example provided as follows: detector 14 receives light through a further diaphragm 13, limited to receive light exiting from perpendicular, optically flat end 10 of plate 3 in an angular range outside the angular range to which detector 11 is limited, and a reference detector 15 to receive light in an intensity related to the effective illumination of the test sample materials by light source 6. A filter is shown in the drawing between the light exit end of the waveguide and the principal detector system, to block light of the excitation wavelength, in manner known per se.

For certain applications it may be desirable to arrange alternative diaphragms in place of those shown in the drawing, so that for example the range of angles of view of detector 11 has not only an upper limit $\alpha$ but also a lower limit $\alpha_1 > 0$ provided by an additional diaphragm or screen, two apertures possibly being provided to give detection of light emerging within the ranges $\pm(\alpha$ to $\alpha_1)$ on either side of the axis direction. In certain embodiments it is possible to dispense with the equivalent of detector 14 and/or detector 15.

A very limited range of angles of view, e.g. of the form $\pm(\alpha$ to $\alpha_1)$, may be appropriate to increase the effective signal to noise ratio in cases where the layer to be optically investigated is of known and well-defined refractive index, or where the angular distribution of the light from surface-bound material is modified to lie in a narrow range of angles, eg. by including a 50 nm silver layer showing surface plasmon resonance on the surface of plate 3 beneath the layer 2: as described by R. E. Benner et al, J.Phys.Chem. 84 (1980), pp 1602–1606.

FIG. 2 of the accompanying drawings shows in diagrammatic graphical form the variation of light output with exit angle in an arrangement such as that of FIG. 1. The horizontal axis of FIG. 2 represents exit angle with reference to the axis (horizontal in FIG. 1) of slide or plate 3, ie. zero angle corresponds to light output along the dotted axis of slide or plate 3 in FIG. 1. The vertical axis represents relative fluorescence intensity, and the several curves of FIG. 2 represent different conditions in the liquid adjacent to slide or plate 3, as follows. Curve 21 shows the dependence of fluorescein (0.5 microgram/ml in water in a 20 micron thick cell space) fluorescence intensity on exit angle, where the fluorescent material is entirely in solution adjacent slide or plate 3. It is apparent that very little fluorescent light exits at angles less than about 45°. Curve 22 shows background signal in one experiment due to binding of bovine serum albumin to slide 3, and curve 23 shows the results of binding fluorescein-labelled protein to slide 3: the fluorescent light output at exit angles close to zero is at a minimum comparable with the background level due to a blank slide as shown by curve 24, and there is a restricted range of exit angle less than about $\alpha$ in which significant light emerges under the conditions of surface-bound fluorescence, although as shown by curve 21 practically no fluorescent light output above background exits in this angular range from the fluorescent substances in solution.

Thus the signal from detector 11 in FIG. 1 can discriminate fluorescence due to surface-bound fluorophor in layer 2 from fluorescence due to fluorophor in the body of liquid 1. The invention is not limited to fluorophors or to fluorescein and its conjugates. Fluorescein is however a particularly convenient fluorophor for use in this invention, as also is rhodamine, eg. used with excitation wavelength 550 nm and emission wavelength 590 nm.

In an alternative embodiment briefly mentioned above, detector 11 as in FIG. 1 can receive the light from a diaphragm with both upper and lower angular limits of its aperture: in this case the light that exits from slide 3 very close to its axis, eg. within about 5 degrees of the axis, is not caught be detector 11. If desired a separate detector of this light can be installed, so that a background level control signal can be derived, and included in the signal processing.

Not shown in the drawings because they constitute per se-conventional structural features, are positive-registration arrangements to mount plate 3 in predetermined alignment relative to the rest of the optical system, overall screening, covering and optical absorbing features to keep out stray light during the measurements, and mechanical means, if required to shift the optics and sample(s) relative to each other, to enable successive measurement of a plurality of samples.

Also not shown in detail are the electrical circuitry and modules, composed of per se conventional units, for taking and processing the signals arising from the detectors 11, 14 and 15 shown in FIG. 1. A schematic block diagram of these arrangements is given in FIG. 3. In one suitable arrangement, the light source 6 of FIG. 1 is a flashlamp 31 (FIG. 3) controlled by controller/power-supply 30: flashlamp 31 illuminates sample cell 4 of FIG. 1 (shown as 32 in FIG. 3).

The light incident on the detectors (11, 14 and 15 in FIG. 1–33, 34 and 35 in FIG. 3) gives rise to electrical signals that are then processed by signal-processing circuitry. This circuitry incorporates any of several known photoelectric signal processing techniques and in particular can incorporate a synchronous lock-in or boxcar detection arrangement actuated by additional signals derived from the reference detector to synchronise with the chopping frequency of the light source. The signals from the detectors are then processed, e.g. by a.c. and d.c. separation, sample-and-hold stages, analogue-to-digital converters, or as may be appropriate, and combined, e.g. by linear combination or ratio circuitry or digital processing, to obtain processed e.g. normalised data signals, or output signals directly representative of any convenient desired parameter. A signal or data output is taken in any desired form, e.g. analogue, digital, graphical, printed or electronically stored or processed data, by the use of appropriate known output or interfacing circuitry and apparatus. Especially, any suitable form of normalisation of the signals from detectors 11 and 14 by reference to detector 15 output can be provided for, and it may be desirable to form combinations, e.g. linear combination or ratios, of the signals from detectors 11 and 14 to give better effective discrimination between the different light sources of interest, subtraction of background light, and/or rejection of changes in the absolute intensity of the pump light. If desired, the circuitry can provide for the making and signal-processing of a succession of light measurements at determined time intervals, to allow the kinetics of the (eg. binding) reactions in the sample cell to be detected or measured.

In the particular arrangement shown schematically in FIG. 3, detector 35 provides timing signals via reset 36 for integrating amplifiers 37 and 38, and gives rise to a delayed trigger signal by delay unit 39 and trigger 40 to control a/d converter 41 which provides a digital output based on the output of analogue divider 42. Typically a suitable ratio signal to be delivered by divider 42 is representative of the ratio of outputs of integrators 37 and 38.

Integrating amplifier 37 thus provides a signal representing the output of the detector of light that exits from waveguide 3 at angles less than $\alpha$, i.e. it is responsive to light from the adsorbed part of the sample material, and integrating amplifier 38 provides a signal representing the output of the detector light that exits from waveguide 3 at angles greater than $\alpha$, i.e. it is responsive to fluorescence from the solution as well as the adsorbed sample material.

This photometer arrangement is provided with all usual suitable screening and cover arrangements to minimise stray light and electrical interference, and suitable holders and registration devices to hold the plate arrangements in predetermined orientation relative to the optical system of the photometer, as well as any desired electronic calibration and stabilisation arrangements to prevent the effects of instrument drift from disturbing the data output in uncontrolled fashion. The sample holder may be present in multiple and movable form and/or the optical system may be movable to subject more than one sample slide to measurement successively.

Where the light source is a flash light-source, it can be useful in certain applications to include arrangements known in themselves for gating the photodetector response open, especially a few microseconds after the flash in order to allow background fluorescence to decay, e.g. as mentioned in Specifications EP No. 0 104 926 and U.S. Pat. No. 4,341,957.

FIG. 4 shows in diagrammatic scheme an optical arrangement for an instrument as in FIG. 1 but with the following modifications. (Like numerals in FIGS. 1 and 4 indicate corresponding parts.) Flash light source 6 is provided with a collimating system 41 to minimise stray light throughput to detectors 11 and 14. A reflective surface 42 is provided opposite the light source to increase the level of illumination on the sample. Detector 15 is shown but may if desired be omitted in this embodiment as alternative means of compensating for excitation light intensity variation and background light is provided by beamsplitter cube 43, detector 44 and the positions of filters 45 and 46 to exclude light of excitation wavelength (as compared with the single filter adjacent waveguide light exit surface 10 in FIG. 1). The light path to detector 44 is transmissive to light of the excitation wavelength and accordingly the signal detector 44 largely represents the intensity of background light exiting from face 10 of the waveguide within the angular range $\pm \alpha$. Filter 45 excludes as much as possible of this light from principal detector 11, and the residual background component of the signal from detector 11 can be largely compensated by a signal derived from detector 44. Detector 14, provided with filter 46 to exclude light of excitation wavelength, can be used to provide a signal to normalise the output from detector 11.

FIGS. 4a and 4b schematically show alternative ways of illuminating the sample cell. In FIG. 4a, light source 6 is surrounded by filter 7 to select light of excitation wavelength, and an elliptical (cylindrical) reflector 47 of which lamp 6 occupies one focus and the sample cell the other focus, to give increased illumination intensity on the sample. In FIG. 4b, light from the source 6 illuminates the sample layer 2 substantially in the plane of layer 2 but substantially transversely of the main direction of propagation of light in the waveguide to the principal detector system (shown here in schematic outline at 48).

It is within the scope of the invention to include as part of layer 2 (FIGS. 1 and 4) in the sample cell a thin metal layer (eg. a silver metal layer about 50 nm thick), formed on the surface of the waveguide 3, and on the surface of which a layer of bound sample material is formed in known manner, eg. as an immunosorbent with attached fluorescently-labelled ligand. This enables the use, in conjunction with the instrumental arrangements described herein, of the per se known phenomenon of surface plasmon resonance (s.p.r.), as described in B. Liedberg et al, Sensors and Actuators, 4 (1983) 299–304, or by Benner et al, cited above, to provide discrimination of sample material bound to layer 2 by means of its effect on the resonant angle at which light energy is maximally dissipated or coupled instead of propagating and exiting through end 10 of waveguide 3. For this purpose, diaphragm 12 can for example be adjusted to a narrow slit width corresponding to an angle near the angle of minimum transmission or coupling due to s.p.r. dissipation or coupling, and detector 11 can then be used to detect changes in light output due to the per se known changes that occur in the s.p.r. angle of maximal dissipation or coupling when sample material becomes bound to layer 2.

This invention is susceptible to any of several variations and modifications within its scope, and extends to the use of any one or more of the singular and several features of the foregoing description and accompanying drawings.

It is also to be noted that many of the devices made and described in our copending application no. 06/834247, claiming priority from our patent application filed on 13th June 1984, G.B. No. 84 15018, and entitled "Devices for Use in Chemical Test Procedures", the entire disclosure of which is hereby incorporated by reference into this present specification, can be usefully applied to carry the test samples to be measured optically by the photometric methods and arrangements described hereinabove.

We claim:

1. A method of optical analysis of a fluorescent test sample which is partly in an aqueous liquid phase and partly bound to an adjacent solid surface, to discriminate the respective bound and liquid parts of said sample, which comprises providing as said solid surface a surface of a transparent solid optical waveguide wherein the waveguide provides one wall of a cell containing the liquid phase of the sample, illuminating the sample directly by a fluorescence excitation source substantially transverse to the axis of the waveguide, and measuring the emitted fluorescent light from the bound sample which has emerged from said waveguide at an angle that deviates from the optical axis of said waveguide by an angle appreciably less than $\alpha$, where $$\alpha = \arcsin\sqrt{(n_2^2 - n_1^2)}$$

where $n_2$ is the refractive index of the material of the waveguide and $n_1$ is the refractive index of the aqueous liquid phase, and excluding from said measurement substantially all light that has emerged from said waveguide at an angle that deviates from said optical axis by $\alpha$ or more.

2. A method according to claim 1 wherein the waveguide is acrylic plastic, the test sample contains fluorescein, and the angle $\alpha$ is about 41°.

3. A method according to claim 1 wherein the waveguide is glass, the test sample contains fluorescein, and the angle $\alpha$ is about 47°.

* * * * *